US006796875B1

(12) United States Patent
Placik

(10) Patent No.: US 6,796,875 B1
(45) Date of Patent: Sep. 28, 2004

(54) BREAST IMPLANT SIZING APPARATUS AND METHOD

(76) Inventor: Otto J. Placik, 2612 Kingston Rd., Northbrook, IL (US) 60062

( * ) Notice: Subject to any disclaimer, the term of this patent is extended or adjusted under 35 U.S.C. 154(b) by 0 days.

(21) Appl. No.: 10/321,901

(22) Filed: Dec. 17, 2002

(51) Int. Cl.[7] .................................................. A41C 3/00

(52) U.S. Cl. .............................................. 450/1; 450/38

(58) Field of Search ................................ 450/1, 54–57, 450/36–38; 623/7, 8

(56) References Cited

U.S. PATENT DOCUMENTS 2,516,129 A * 7/1950 Leo et al. ..................... 450/38
2,597,924 A * 5/1952 Davenport et al. ........... 450/38
2,697,229 A * 12/1954 Krueger ....................... 450/38
2,725,633 A 12/1955 Graf
2,826,202 A 3/1958 Star
2,842,775 A * 7/1958 Pangman ....................... 623/7
3,559,214 A * 2/1971 Pangman ....................... 623/7
3,600,718 A 8/1971 Boone
4,024,856 A 5/1977 Kirianoff
4,095,295 A 6/1978 Lake
4,219,029 A 8/1980 Grossman et al.
4,263,682 A * 4/1981 Bejarano ....................... 623/7
4,338,953 A 7/1982 Ward
4,624,671 A 11/1986 Kress
5,037,436 A 8/1991 Heaston
5,347,656 A 9/1994 Fabritz et al.
5,496,345 A 3/1996 Kieturakis et al.
5,549,672 A 8/1996 Maddock et al.
5,823,852 A * 10/1998 Chu ............................ 450/38
5,833,515 A 11/1998 Shahbazian et al.
6,055,989 A 5/2000 Rehnke
6,132,288 A * 10/2000 Aerts .......................... 450/38
6,302,760 B1 * 10/2001 Dai ............................ 450/38

* cited by examiner

*Primary Examiner*—Gloria Hale

(57) ABSTRACT

A system for sizing surgically implantable human breasts prostheses includes a disposable brassiere-like garment having two breast-receiving cups of predetermined size and shape, each having a pocket formed on an inner surface thereof. Disposable inflatable, flexible and resilient bladders are respectively receivable in the pockets and may be inflated and/or deflated with an associated disposable graduated syringe, either before or after insertion in the pockets.

14 Claims, 4 Drawing Sheets

40 34 36 35 33 31 32 28 27 11 10 26 25 14

BREAST IMPLANT SIZING APPARATUS AND METHOD

BACKGROUND

This application relates to methods and apparatus for accurately sizing surgically implantable breast prostheses prior to implantation.

Surgical implantation of material in human female breasts has become fairly common, both for medical reconstructive and for cosmetic purposes. A key factor in such surgery is the proper selection of the size of the prosthetic implant. Currently, patients and physicians typically make their choices based on anatomic factors or using crude and unwieldy devices, such as tape measures.

One prior technique, disclosed in U.S. Pat. No. 4,024,856, uses a concave template of fixed size and shape placed around the breast and releasably sealed to the chest. A liquid is injected into the space between the breast and the template. From a measurement of the volume of liquid injected, the breast volume could be calculated. However, it has been found difficult to effect a perfect fluid-tight seal of the template to the chest.

Another technique, disclosed in U.S. Pat. No. 4,624,671, involves surgically implanting an empty, inflatable elastomeric balloon in the breast, filling the balloon with a liquid to the desired size, measuring the amount of liquid in the filled balloon and then removing the liquid from the balloon and removing the balloon from the breast. However, this technique must be performed at the time of surgical implantation of the prosthesis, or would require two separate surgical procedures.

The manufacturers of implantable prostheses provide "sizers," which are essentially inflatable mock-ups of the implantable prostheses themselves, which can be inflated with air or water and inserted in the patient's own brassiere, these mock-ups respectively corresponding in size to the available sizes of implants. However, these mock-ups are relatively expensive and, in order to permit a patient to test various sizes at home, it would be necessary to provide the patient with a number of different-size mock-ups, and many patients are unwilling to incur that additional expense. It would be possible to "lend" the mock-ups to the patient, but this would raise sterility issues upon return of the mock-ups, which issues are of concern to many patients who would be unwilling to reuse a previously-used mock-up. It is also possible to perform the sizing test procedure in the physician's office, but this is undesirable because of time constraints. It is preferable that the patient be able to test different sizes at her leisure at home.

Applicant has attempted to minimize costs by instructing patients to utilize water-filled receivable plastic bags or rice-filled nylon stockings instead of the commercial "sizers." These latter techniques have improved patient input in the implant decision-making process. However, due to the lack of sophistication of these techniques, outcomes may still be less than optimal.

SUMMARY

This application describes a technique for accurately sizing surgically implantable human breast prostheses which avoids the disadvantages of prior techniques while affording additional structural and operating advantages.

An aspect of the technique is that it is simple and economical.

In connection with the foregoing aspect, the technique uses low-cost, disposable apparatus.

Another aspect is that it affords precision without risk of fluid spillage and without discomfort or risk to the patient.

In an embodiment, there is provided an apparatus for sizing a surgically implantable human breast prosthesis comprising: a disposable brassiere-like garment including at least one elastic breast-receiving cup of a predetermined size and shape and having an inner surface, a pocket formed on the inner surface of the at least one cup, and at least one disposable, inflatable, flexible and resilient bladder removably receivable in the pocket and having a fluid inlet/outlet port for inflation and deflation of the bladder.

There is also provided a method of utilizing an apparatus of the type set forth, involving removably inserting a bladder into a pocket in a cup of a brassiere-like garment and introducing a fluid into the bladder for inflating the bladder.

Fluid may be introduced into and removed from the bladder by the use of a syringe coupled to the bladder via suitable fittings.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

DETAILED DESCRIPTION

Figure 1:
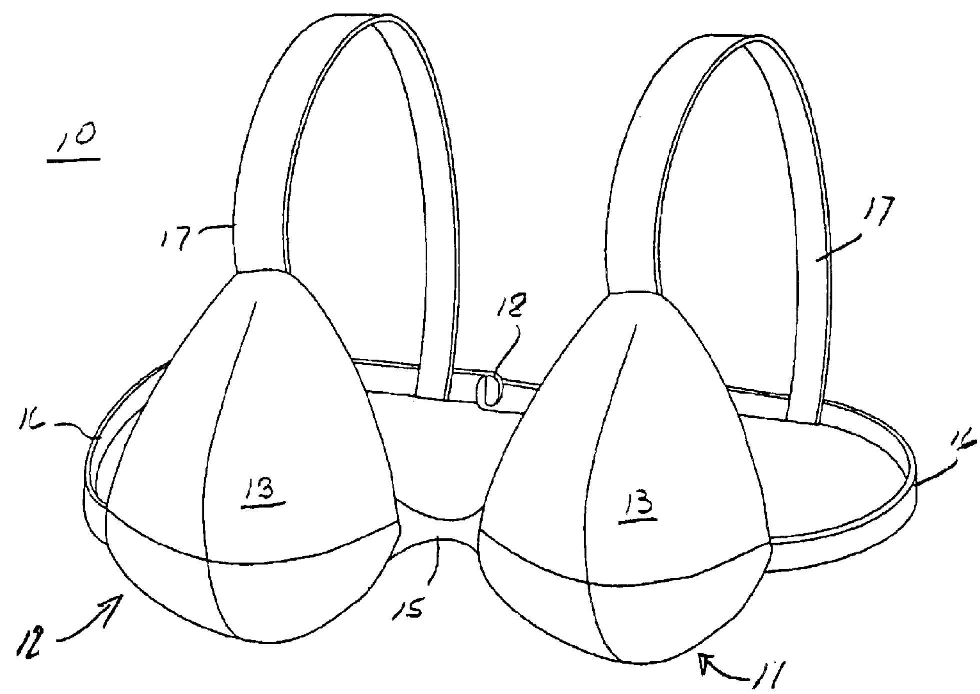
FIG. 1 is a front perspective view of a brassiere-like garment for use in the disclosed technique.
Figure 2:
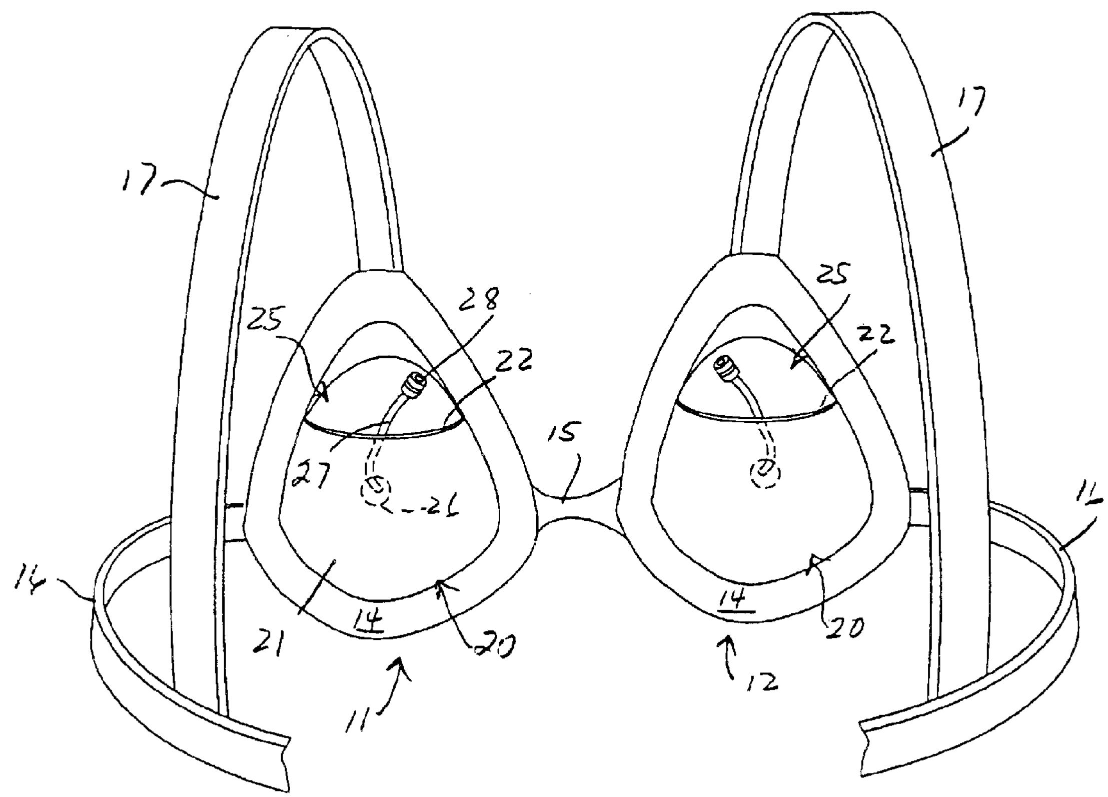
FIG. 2 is a fragmentary rear elevational view of the garment of FIG. 1, illustrating bladders inserted in the cup pockets.
Figure 3:
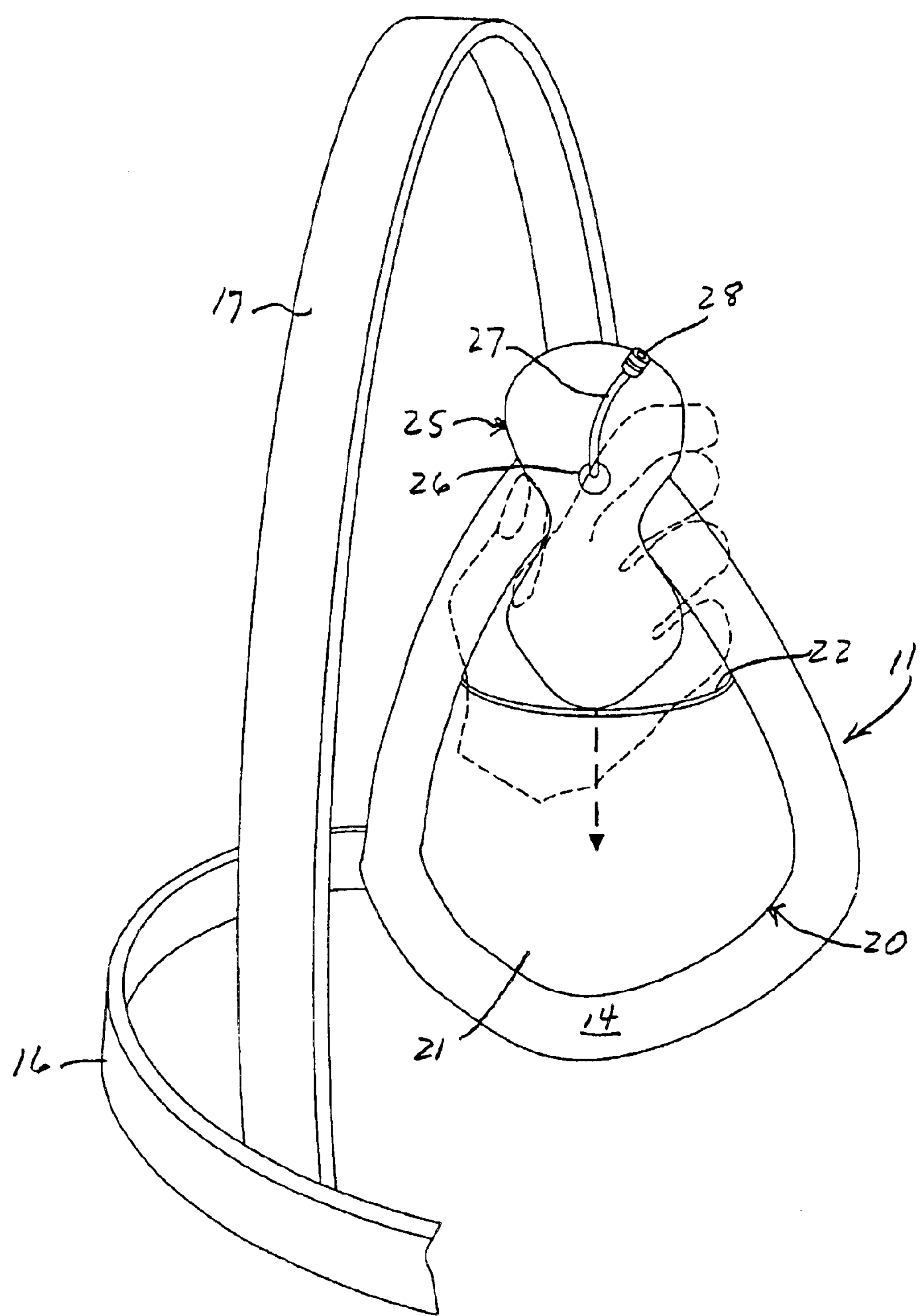
FIG. 3 is an enlarged, fragmentary view of a portion of FIG. 2 illustrating the insertion of the bladder into the pocket.
Figure 4:
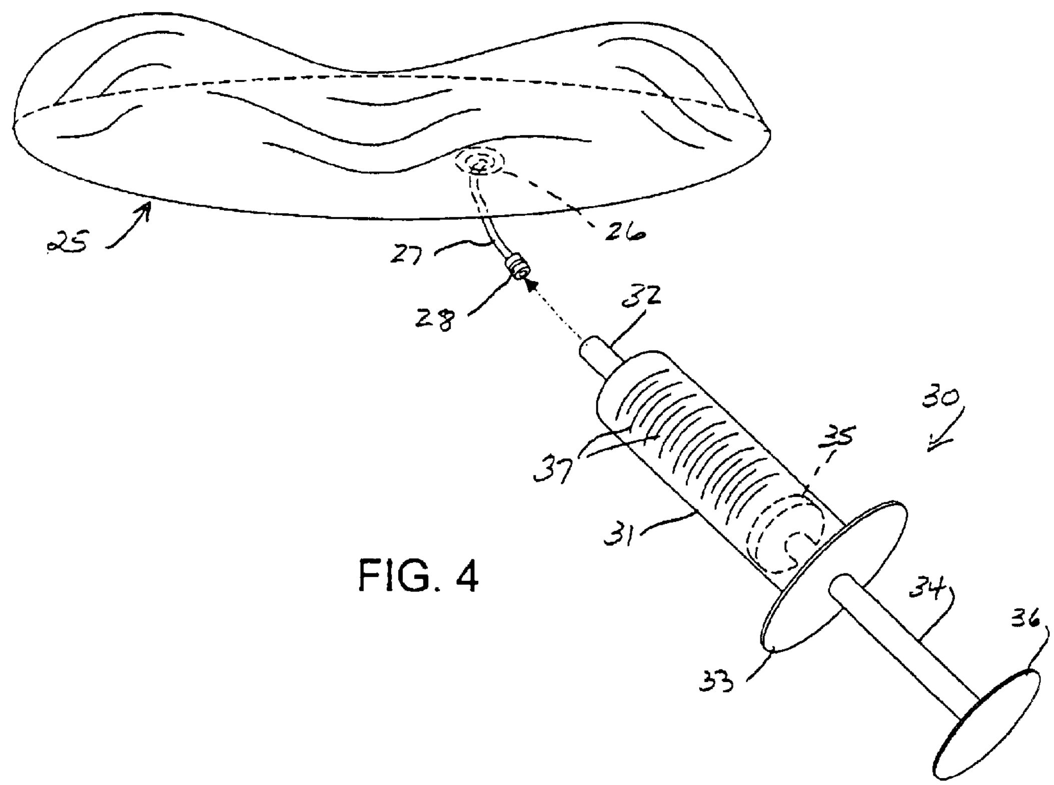
FIG. 4 is an enlarged perspective view of a bladder and associated syringe illustrating the coupling of the syringe with the bladder.
Figure 5:
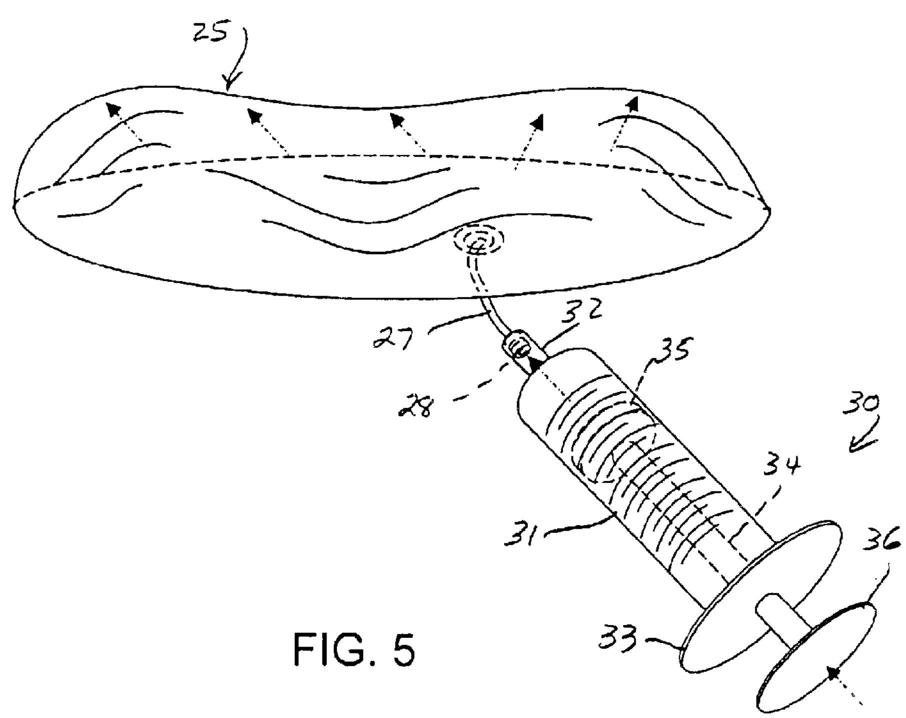
FIG. 5 is a view similar to FIG. 4 illustrating inflation of the bladder while it is outside the garment pocket.

Referring to the drawings, there is illustrated a garment 10, inflatable bladders 25 and a fluid-moving syringe 30 which cooperate to form a system 40. Referring in particular to FIGS. 1-3, the garment 10 is a brassiere-like garment having two breast-receiving cups 11 and 12 which may be formed of a suitable expansible elastic fabric. Each cup has an outer surface 13 and an inner surface 14, the cups may be joined adjacent to their rear edges by a bridge 15, which may also be formed of an elastic material. The garment 10 is provided with two elastic backstraps 16, respectively connected to the laterally outer edges of the cups 11 and 12 and each connected, intermediate its ends, to one end of a shoulder loop 17, the other end of which is connected to the upper edge of the associated cup. The distal ends of the backstraps 16 may respectively terminate in hooks 18 for securing them together in a known manner, and/or similar hooks may be provided at the location of the bridge 15. Alternatively, hooks may be provided at neither location and the garment may be of the slip-on type.

Each of the cups 11 and 12 is provided on its rear surface with a pocket 20, which may be formed from a sheet or patch 21 of suitable fabric, which may be fixedly secured by suitable means, such as stitching or bonding, along most of its periphery to the inner surface 14 of the associated cup, leaving a free upper edge 22 to provide an access opening into the pocket. Alternatively, instead of a continuous sheet 21 of fabric, the pocket 20 may be formed with a mesh or net-type material or by the use of plural straps or bands of material. The pockets 20 may also be formed of a suitable elastic material. The materials and method of construction of the garment 10 are inexpensive so that the garment 10 may be disposable.

Referring to FIGS. 2-7, each bladder 25 is in the nature of an inflatable, flexible and resilient membrane, which is formed of a suitable elastic and fluid-impermeable material. As will be explained more fully below, a number of such bladders may be provided. A wide variety of materials would be suitable for forming the bladders 25, such as neoprene, vinyl, latex and the like, but preferably a relatively inexpensive material would be selected so that the bladders 25 may be disposable. Each bladder 25 is completely closed except for a port 26 which is connected to the proximal end of a tube 27, the distal end of which is provided with a coupling fitting 28 for providing access to a source of fluid for introducing fluid into the bladder 25 for inflating it or removing fluid from the bladder 25 for deflating it. Typically, before inflating a bladder, the user would first make sure that all air or other fluid is exhausted from the bladder 25, either by completely flattening the bladder or, alternatively, by withdrawing air or other fluid from the bladder with an inflation/deflation device, such as the type described below. Alternatively, the bladder 25 could also be provided with a second port and associated tube (not shown) so that, as fluid is inserted through one port, air or other residual material in the bladder is exhausted through the other port, thereby facilitating ensuring that the bladder is filled only with the inflating fluid. It is contemplated that a number of different sizes of bladder 25 may be provided, but each is dimensioned and shaped to be receivable in one of the pockets 20, as illustrated in FIGS. 2 and 3.

Referring to FIGS. 4-7, inflation and deflation of the bladder 25 is effected by means of a suitable apparatus, such as a syringe 30, which may be formed of a suitable inexpensive plastic material so as to be disposable. The syringe 30 has an elongated cylindrical tube 31, which may be transparent or translucent to permit viewing of the contents thereof, the tube 31 being closed at one end by a circular end wall (not shown) having a central opening to which is connected one end of a narrow cylindrical fitting 32 adapted for fluid-tight coupling to the fitting 28 of the bladder 25. The other end of the tube 35 is closed by an end cap 33 having a central opening therein through which is received an elongated piston rod 34. The inner end of the rod 34 is connected to a disc-like circular plunger 35 adapted to slide along the inner surface of the tube 31 in a substantially fluid-tight sealing manner. The outer end of the rod 35 is connected to a handle 36. The tube 31 may be provided with suitable graduation indicia 37 to permit ready measurement of the volume of the contents of the tube 31.

In use, it is contemplated that a patient would be provided with the system 40 in the form of a disposable "kit", including a suitably-sized garment 10, a syringe 30, and one or more pairs of bladders 25, each pair being of a different size, or maximum inflation capacity or volume. The patient would be instructed to, at her leisure at home, wear the garment 10 and insert in the pockets 20 one pair of bladders 25, e.g., the smallest sized pair provided. Then, utilizing the syringe 30, the user would inflate the bladders 25 to a desired size. In this regard, the bladders 25 could be filled with air or water. In the former case, the user would simply withdraw the rod 34 until the plunger 35 is as close as possible to the end cap 33, thereby allowing the tube 31 to fill with air. Then, the syringe fitting 32 is coupled to the bladder fitting 28 and the handle 36 is depressed to move the plunger 35 toward the fitting 32, driving air into the bladder 25 to inflate it. If water or another liquid were utilized for inflation, the plunger 35 would first be fully depressed until it is as close as possible to the fitting 32. Then the fitting 32 would be immersed in the liquid and the plunger withdrawn to draw the liquid into the tube 31. Then, with the fitting 32 elevated, it would be coupled to the bladder fitting 28 and the liquid then injected into the bladder 25 to inflate it to the desired level. In either case, a patient would simply try different inflation levels until a suitable one was found. If the maximum inflation capacity of a bladder 25 is reached without achieving a desirable size, the user would then proceed to the next size of bladder and proceed as before. When the desired bladder size and inflation level have been determined, the user would carefully note the volume of fluid injected to achieve this inflation level and report the bladder size and injected volume of fluid to the physician. The system 40 may be discarded when it is no longer needed.

Figure 6:
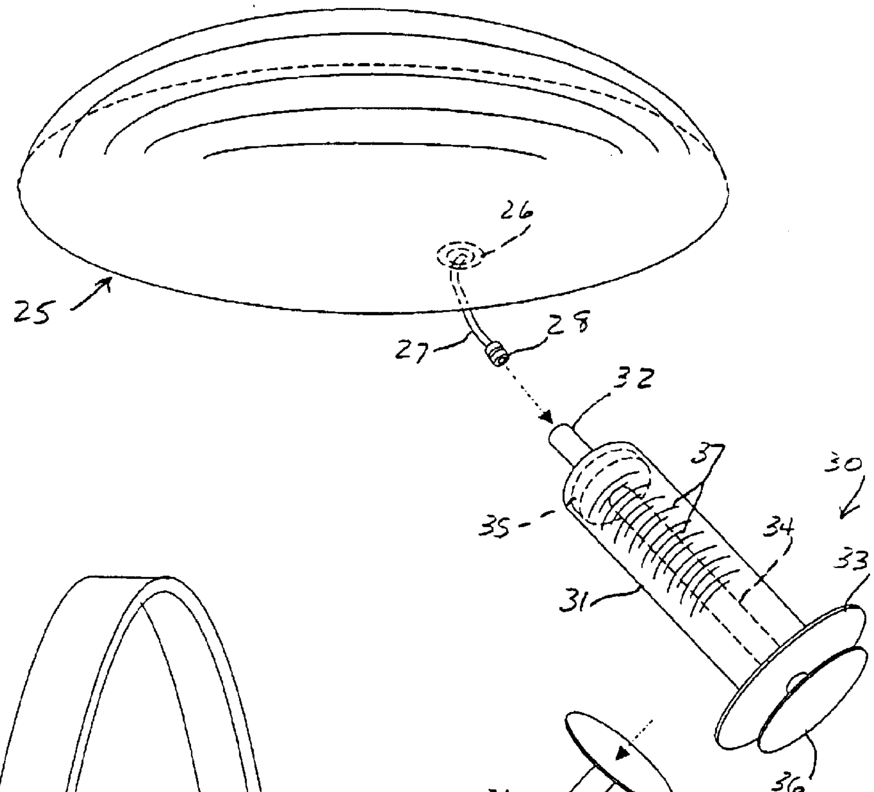
FIG. 6 is a view similar to FIG. 4 illustrating deflation of the bladder while it is outside the garment.
Figure 7:
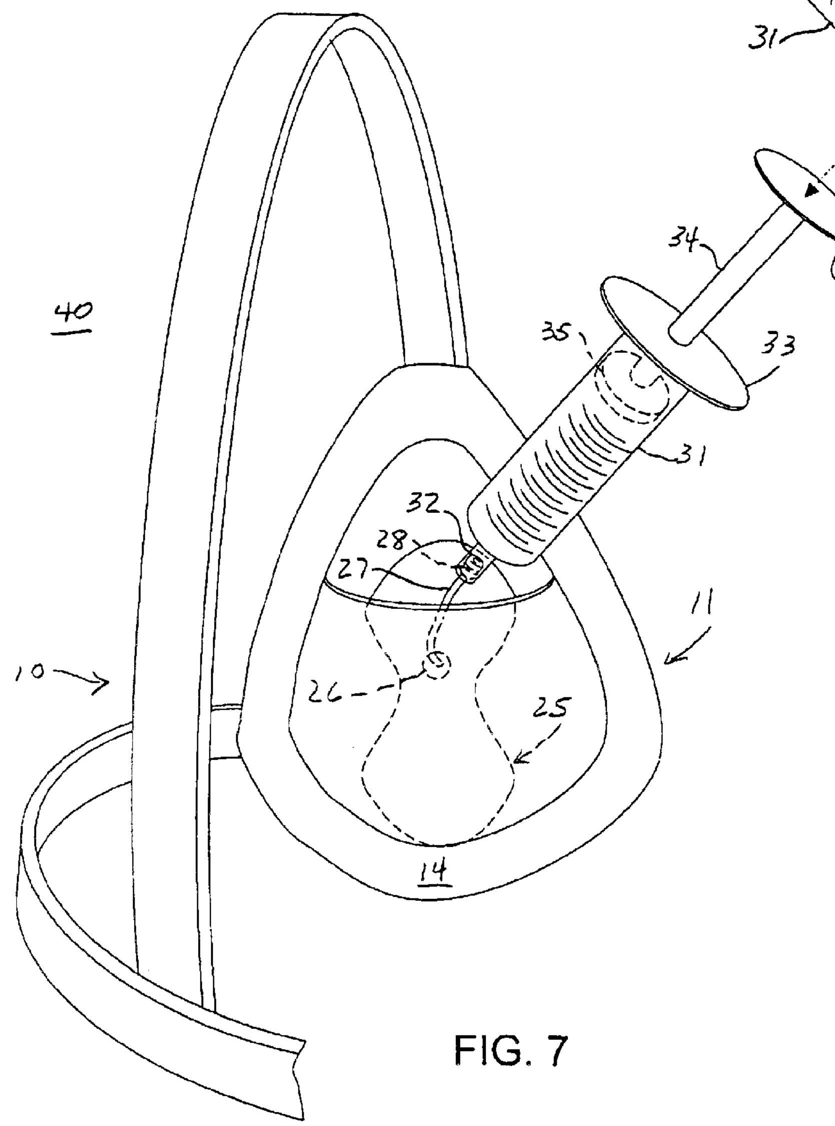
FIG. 7 is a view similar to FIG. 3 illustrating use of the syringe to inflate the bladder while it is disposed in the garment pocket.

A significant aspect of the system 40 is that, by providing individual bladders 25 in the cups 11 and 12, the patient can, in the event of different-sized breasts, arrive at different inflation levels to achieve a uniform breast size after implantation. It will be appreciated that the elastic cups 11 and 12 will expand as necessary, to accommodate the inflation of the bladders 25. Referring to FIG. 6, it will be appreciated that the syringe 30 may also be used to withdraw fluid from a bladder 25, thereby deflating it to ensure that it has been completely exhausted before inflation. In this way, the volume of fluid used to inflate the bladder 25 can be accurately measured.

From the foregoing, it can be seen that there has been provided an improved apparatus and method for sizing of surgically implantable human breast prostheses, which involves the use of an inexpensive, disposable kit, which can easily be used by a patient at her leisure at home, and is safe and effective.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicant's contribution. The actual scope of the protection sought is intended to be defined in the following claims when viewed in their proper perspective based on the prior art.

What is claimed is:

1. A low-cost, disposable kit for use by a candidate for surgical implantation of a breast prosthesis to determine the proper size of the prosthesis, the kit comprising:

a disposable brassiere-like holder including at least one elastic breast-receiving cup of a predetermined size and shape and having an inner surface, a pocket formed on the inner surface of the at least one cup, a plurality of disposable, inflatable, flexible bladders removably receivable one-at-a-time in the pocket, the bladders being respectively of different sizes to as to be respectively inflatable to different maximum volumes, each bladder having a fluid inlet/outlet port for inflation and deflation of the bladder, and a disposable inflation/deflation device adapted to be coupled to the port for introducing fluid into the bladder for inflating the bladder and removing fluid from the bladder for deflating the bladder.

2. The kit of claim 1, wherein the at least one cup includes two cups each having a pocket formed on the inner surface thereof, the bladders being removably receivable one-at-a-time in each of the pockets.

3. The kit of claim 1, wherein the pocket has an open top.

4. The kit of claim 3, wherein the pocket is formed by a sheet of material fixedly secured around a portion of its periphery to the inner surface of the cup.

5. The kit of claim 1, wherein each bladder includes a tube extending from the port and communicating therewith and a first coupling fitting carried by a distal end of the tube.

6. The kit of claim 5, wherein the inflation/deflation device has a second coupling fittings adapted to be coupled to the first coupling fitting in a fluid-tight manner.

7. The kit of claim 1, wherein the inflation/deflation device includes a graduated syringe.

8. A method by which a candidate for surgical implantation of a breast prosthesis can determine the proper size of the prosthesis, the method comprising:

(a) providing a disposable brassiere-like holder including at least one elastic breast-receiving cup of a predetermined size and shape with a pocket formed on an inner surface of the cup, (b) providing a plurality of disposable, inflatable, flexible bladders respectively of different sizes so as to be respectively inflatable to different maximum volumes, (c) removably inserting a first bladder in the pocket, (d) introducing a fluid into the first bladder for inflating the first bladder to a desired volume or until the maximum volume is reached without reaching the desired volume, (e) if, at step (d), the maximum volume is reached without reaching the desired volume, then deflating and removing the first bladder and repeating steps (c) and (d) with different bladders until the desired volume is reached, and (f) when the desired volume is reached noting the bladder size and the amount of fluid required to inflate the bladder to the desired volume.

9. The method of claim 8, wherein the fluid is a liquid.

10. The method of claim 9, wherein the liquid is water.

11. The method of claim 8, wherein the bladder is inflated before insertion into the pocket.

12. The method of claim 8, wherein the bladder is inflated after insertion into the pocket.

13. The method of claim 8, wherein the introducing includes utilizing a graduated syringe to inflate the bladder.

14. The method of claim 8, wherein step (a) includes providing a disposable brassiere-like holder including two elastic breast-receiving cups, each of a predetermined size and shape and each with a pocket formed on an inner surface thereof, steps (c)–(f) being performed with respect to each cup.

* * * * *